United States Patent
Wu et al.

(10) Patent No.: US 8,506,766 B2
(45) Date of Patent: Aug. 13, 2013

(54) METHOD FOR RECOVERY OF ACETIC ACID FROM AN AQUEOUS SOLUTION THEREOF

(75) Inventors: Kuang-Yeu Wu, Plano, TX (US);
Ji-Young Jang, McKinney, TX (US);
Karl Tze-Tang Chuang, Edmonton (CA)

(73) Assignee: AMT International Inc., Plano, TX (US)

( * ) Notice: Subject to any disclaimer, the term of this patent is extended or adjusted under 35 U.S.C. 154(b) by 0 days.

(21) Appl. No.: 13/573,416

(22) Filed: Sep. 14, 2012

(65) Prior Publication Data

US 2013/0012738 A1    Jan. 10, 2013

Related U.S. Application Data

(62) Division of application No. 12/382,801, filed on Mar. 24, 2009, now Pat. No. 8,268,131.

(51) Int. Cl.
*B01D 3/36* (2006.01)
*B01D 3/34* (2006.01)
*B01D 3/06* (2006.01)
*C07C 51/46* (2006.01)
*C07C 51/48* (2006.01)
*C07C 51/50* (2006.01)
*C07C 53/08* (2006.01)

(52) U.S. Cl.
USPC ............. 203/16; 203/29; 203/42; 203/43; 203/46; 203/60; 203/87; 203/88; 203/98; 203/DIG. 9; 203/DIG. 16; 562/607; 562/608

(58) Field of Classification Search
USPC ............. 159/2.1, 44, 47.1; 203/3, 16, 29, 203/41–46, 60, 87, 88, 98, DIG. 9, DIG. 16; 562/607, 608; 568/913, 916
See application file for complete search history.

(56) References Cited

U.S. PATENT DOCUMENTS

| | | | | | |
|---|---|---|---|---|---|
| 2,395,010 | A | * | 2/1946 | Othmer | 562/608 |
| 3,350,445 | A | * | 10/1967 | Binning et al. | 562/548 |
| 3,412,160 | A | * | 11/1968 | Schierholt | 568/868 |
| 3,433,831 | A | * | 3/1969 | Aoshima et al. | 562/600 |
| 4,353,784 | A | * | 10/1982 | Koga et al. | 203/16 |
| 5,187,309 | A | * | 2/1993 | Esch et al. | 560/218 |
| 5,492,603 | A | * | 2/1996 | Gualy et al. | 202/158 |
| 5,492,625 | A | * | 2/1996 | Wytcherley et al. | 210/634 |
| 5,686,630 | A | * | 11/1997 | Miao et al. | 549/274 |
| 6,028,215 | A | * | 2/2000 | Bessling et al. | 560/265 |
| 6,399,812 | B1 | * | 6/2002 | Yan et al. | 560/231 |
| 6,793,777 | B1 | * | 9/2004 | Rudinger et al. | 203/14 |
| 7,048,835 | B2 | * | 5/2006 | Jang et al. | 203/16 |
| 7,601,865 | B2 | * | 10/2009 | Verser et al. | 562/508 |
| 2005/0272951 | A1 | * | 12/2005 | Noe' | 562/412 |
| 2007/0129564 | A1 | * | 6/2007 | Schwalm et al. | 560/4 |

* cited by examiner

*Primary Examiner* — Virginia Manoharan
(74) *Attorney, Agent, or Firm* — George A. Seaby

(57) ABSTRACT

A method for recovering acetic acid from an aqueous feed stream containing acetic acid and, in particular, a stream generated during terephthalic acid production includes feeding a water-rich feed stream to a liquid-liquid extraction column, which includes a guard bed near the top thereof for conversion of alcohol within the feed stream by reaction with acetic acid to the corresponding ester, and removing residual water from acetic acid in an azeotropic distillation column by feeding water-poor feed streams from the extraction column to the distillation column at a height at which the mixture has a similar water concentration. The liquid-liquid extraction column produces an extract of an extraction solvent and acetic acid which is sent to the azeotropic distillation column to separate residual water and acetic acid.

10 Claims, 3 Drawing Sheets

METHOD FOR RECOVERY OF ACETIC ACID FROM AN AQUEOUS SOLUTION THEREOF

This is a divisional of application Ser. No. 12/382,801, filed Mar. 24, 2009 and issued as U.S. Pat. No. 8,268,131 on Sep. 18, 2012.

BACKGROUND OF THE INVENTION

This invention relates generally to reduction of energy consumption in chemical processes used in the distillation of industrial chemicals, and in particular to distillation systems and methods for the recovery of acetic acid from aqueous solutions. The present invention is particularly suited for the recovery of acetic acid used in the production of terephthalic acid.

Terephthalic acid is useful in a diverse variety of industrial applications and chemical processes. For example, terephthalic acid is a starting material for producing polyesters including plastic and Dacron™ polyester used in textile and container production. Polyethylene terephthalate (PET) is a form of polyester or Mylar™ that is an extremely tough resin and useful in many industrial and consumer applications. Soft drink and water bottles are made from this resin in addition to plastic jars and clamshell packages used in consumer good transport and food distribution. Purified terephthalic acid is a higher grade of terephthalic acid which is used for finer industrial applications.

Terephthalic acid typically is produced by reaction of par-axylene with molecular oxygen in the presence of a catalyst. During the production process, acetic acid is used as a solvent of terephthalic acid. The acetic acid becomes diluted in water during the oxidation in a reactor section of a terephthalic acid plant in the production cycle. A portion of the acetic acid and water containing stream is then sent to a dehydration unit to remove the water generated in the reactor for recycling or waste.

Three different approaches have been employed in the terephthalic acid plants to separate the acetic acid and water so that the acetic acid can be recycled back to the reactor while the water generated by the reaction is sent to the wastewater treatment facility for safe disposal. One approach is by conventional distillation wherein the different boiling point of the components provides for the separation of acetic acid and water. In an azeotropic distillation approach, entrainers are used to form azeotropes with the acetic acid and water providing for a change in energy requirements for processing. Liquid-liquid extraction is a final approach for acetic acid and water separation during the terephthalic acid production.

Distillation has been widely used as a primary unit operation for acetic acid recovery from water. In such processes, one or more towers are utilized to process a number of streams of varying concentration of acetic acid with the purpose of recovering it for further use in the oxidation reactor. The products from the distillation tower are a bottom stream of concentrated acetic acid and an overhead stream that ideally would be pure water to minimize the loss of the valuable acetic acid solvent. A more pure overhead water stream would also reduce the burden on downstream wastewater treatment facilities thereby preventing accidental chemical spills.

However, the distillation of acetic acid and water is not very efficient due to the close-boiling characteristics of the acetic acid/water system. Conventional distillation systems require the use of a high number of theoretical stages, i.e., actual trays, and a high reflux ratio, i.e., high energy consumption, to obtain reasonably low levels of acetic acid, typically in the range of 0.4-0.8 wt % in the overhead distilled water. The distillate is subsequently processed to recover certain organic by-products, and then sent to the wastewater treatment facility where any remaining acetic acid is neutralized and spent.

The use of conventional distillation, therefore, involves high investment cost because of the required large size of equipment and high operating cost because of high steam consumption. Furthermore, the traditional process scheme does not allow one to economically obtain a distillate low in acetic acid concentration. This limitation, in turn, presents operating problems including costs associated with the operation resulting from the acetic acid losses, costs associated with the treatment of the acetic acid in the wastewater, limitations of the capacity of the downsteam wastewater treating facility and environmental problems that are continually increasing because of the ever more rigorous standards for acceptable levels of emission to the environment.

There has been an effort to look for alternative processes to minimize the high operating costs associated with the conventional distillation for the separation of acetic acid and water. Chemical processors and companies have resorted to azeotropic distillation involving the addition of selective alkyl acetate, such as the isobutyl acetate, normal butyl acetate, normal propyl acetate, etc., as an entrainer to the azeotropic dehydration column. The entrainer forms a low boiling azeotrope with water and therefore improves the relative volatility for the separation between the acetic acid containing stream and the alkyl-acetate/water azeotrope. This reduces the energy and theoretical stage requirements for the same separation. Compared to the conventional distillation, an azeotropic distillation approach typically reduces the energy (i.e. steam) consumption by 20-40% at the acetic acid/water dehydration column while giving relatively low acetic acid concentration, 300-800 ppm, in the distilled water. The azeotropic distillation column is generally operated at ambient pressure in the terephthalic acid manufacturing plants in all prior art systems.

Other methods used in terephthalic acid production include the use of liquid-liquid extraction with special extractive agents to recover the acetic acid from the water streams so that the residual concentration is reduced to 0.1 wt % to 2.0 wt % acetic acid. Some of the agents usually are acetates, amines, ketones, phosphine oxides, and mixtures thereof. These agents are used as solvents such that they dissolve one component preferentially, allowing the other component to leave at the top of the extraction column. Once the extraction step is completed, a complicated series of distillation steps is required to recover the acid and to recirculate the solvent back to the extraction column.

Such extraction and azeotropic distillation processes for recovery of acetic acid from aqueous streams are described, for example, by Othmer in U.S. Pat. No. 2,395,010 (1946) and Sasaki et al in U.S. Pat. No. 5,662,780 (1997) and have been applied to the recovery of acetic acid from manufacture of terephthalic acid as described, for example by Ohkoshi et al in Japanese Patent Application JP 244196/95 (1995) and European Patent Application EP 0 764 627.

However, these processes are still energy intensive, and it is desirable to further reduce energy consumption in recovery of acetic acid from such streams.

SUMMARY OF THE INVENTION

According to the invention, an extraction and distillation apparatus for recovering acetic acid from an aqueous solution thereof, e.g., during terephthalic acid production is disclosed comprising an extraction column, an azeotropic distillation column for dehydration of the extractant, and a plurality of input feed streams containing various concentrations of acetic acid and water mixtures. The extraction column is a liquid-liquid contacting device and is located upstream from and in fluid communication with the azeotropic distillation column.

In one embodiment, the new apparatus also includes separate locations for feed streams into the azeotropic distillation and liquid-liquid extraction columns, respectively, for the different water-poor (below about 50%) and water-rich (above about 50%) streams containing acetic acid.

In another embodiment, a guard bed is provided within the extraction column.

In yet another embodiment, the new apparatus further comprises a pre-concentrator for providing more concentrated aqueous acetic solutions to both the liquid-liquid extractor and the azeotropic distillation column.

According to a process aspect of the invention, the aqueous stream fed into the extraction column is contacted with an extraction solvent into which acetic acid is extracted thus substantially reducing the concentration of acetic acid in the water stream. Preferably, the extraction solvent is selected from a group of isobutyl acetate, normal butyl acetate, isopropyl acetate, and ethyl acetate. An azeotropic mixture comprising water and, preferably, an ester that is the same ester as the extraction solvent is distilled from the top of the azeotropic distillation column, and an acetic acid rich liquid stream is recovered from the bottom of said azeotropic distillation column.

It has also been found that there is a tendency for the concentration of the alcohol produced by hydrolysis of the ester to build up during operation of the process, necessitating either separation or destruction of said alcohol, thereby reducing the overall efficiency of the process and increasing costs of operation.

Accordingly, a guard bed is installed in the extraction column to prevent build up of the amount of alcohol that is hydrolyzed from the acetates in the process. The alcohol is esterified in the guard bed to the corresponding acetate, thus keeping the alcohol content, and therefore the acetate content in the process at a constant level, improving the efficiency of the separation process.

In another embodiment of the invention, water-poor and water-rich streams are fed at different locations of the liquid/liquid extraction column to improve the efficiency of the separation process and thereby reduce energy consumption.

In yet another embodiment, water-poor streams are fed directly to the azeotropic distillation column, each stream being fed at a height in said column at which the aqueous mixture within said column has a similar water concentration.

The net effects of incorporating one or more of these features, preferably together, are to improve the overall efficiency of the process for separation and recovery of acetic acid from aqueous streams to substantially reduce energy consumption for the overall terephthalic acid production processes.

Further, the distillation apparatus and process described herein are compatible with existing terephthalic acid manufacturing systems so that the invention may be readily installed to enhance existing plants without large capital expenditures.

DETAILED DESCRIPTION OF THE INVENTION

Herein, conventional tower internals refers to various types of trays, packings and the like. Conventional distillation refers to a conventional distillation tower without the use of entrainers or solvents in the separation of the chemicals. Azeotropic distillation refers to distillation utilizing an entrainer to separate the chemicals. An entrainer is a mass separating agent used to separate a mixture by forming a lower boiling azeotrope with at least one of the components in that mixture, in this case an azeotropic mixture of water and the entrainer.

What is needed is a more energy efficient distillation system for recovery of acetic acid from streams also containing water, which produces less waste and unwanted byproducts than prior art systems. Preferably, the distillation system and process should be compatible with existing terephthalic acid manufacturing systems so that it may be readily installed to enhance existing plants without large capital expenditures.

All liquid streams, without limitation to acetic acid concentration, can be sent to the liquid-liquid extractor, whereas vapor streams which cannot be fed to the liquid-liquid extraction column are sent directly to the azeotropic column.

Large amounts of energy are expended within prior art systems for recovery of acetic acid from aqueous streams effluent from processes for production of terephthalic acid.

Figure 1:
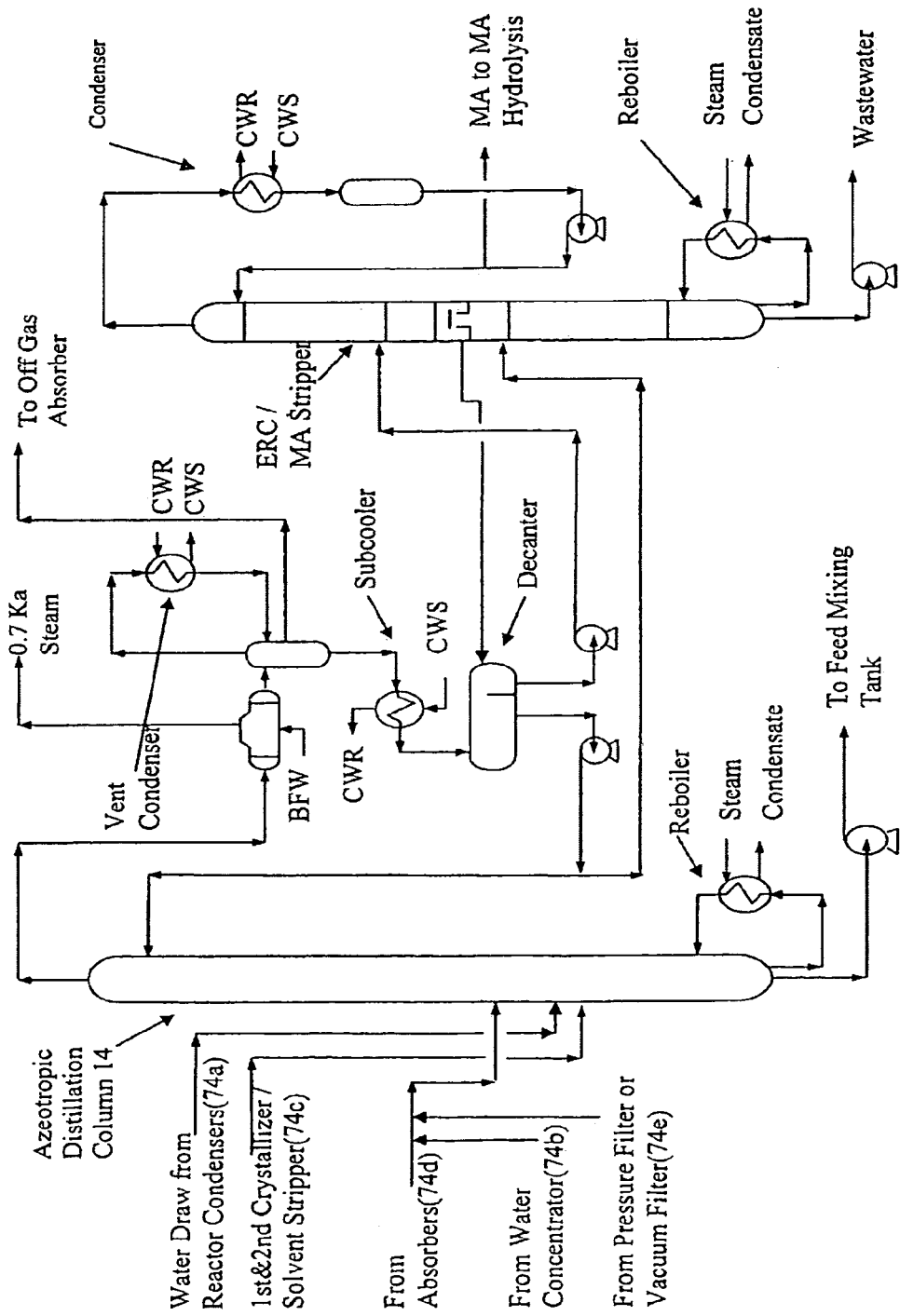
FIG. 1 is an illustrative flow sheet for a PRIOR ART process using acetates for separation by azeotropic distillation of water from acetic acid containing streams.

An exemplary process for production of terephthalic acid is shown in prior art FIG. 1, taken from Jang et al, U.S. Pat. No. 7,048,835 (2006). In addition to the energy expenditures at such plants, minimal to no recycling occurs where solvents such as acetic acid are not recovered and are sent to wastewater treatment facilities, thereby increasing the energy requirements by requiring further processing outside the scope of the plant system.

There are several streams of effluent $74a$, $74b$, $74c$, $74d$, $74e$ containing both water and acetic acid emanating from terephthalic acid production facilities, as illustrated in FIG. 1, including relatively water-poor streams (water content up to about 50%) $74a$, $74b$, $74c$ and water-rich streams (water content typically over-50%) $74d$, $74e$. Water-poor streams $74a$, $74b$, $74c$ are drawn from reactor condensers and crystallizers/solvent strippers. Water-rich streams $74d$, $74e$ are drawn from absorbers, and include the water draw distillate and the wash water from press filters.

Referring again to FIG. 1, while it is possible to use an azeotropic distillation column 14 alone to partly separate water and acetic acid, for example by use of an alkyl-acetate entrainer to form an acetate-water azeotrope, this method has high demand for energy and is less efficient than other methods, especially for high water concentration streams.

Terephthalic acid typically is produced by reaction of paraxylene with molecular oxygen in the presence of catalysts in a system such as, that illustrated in FIG. 1, of U.S. Pat. No. 7,048,835 (2006) by Jang et al, and the process described by Ohkoshi et al in Japanese Patent Application JP 244196/95 (1995) and European Patent Application EP 0 764 627 (1996). There are several different examples of such processes, the essential components of which may be common to different manufacturing plants. During the production process, acetic acid is used as a solvent of terephthalic acid. The acetic acid becomes diluted in water generated during the oxidation reaction in a reactor of the terephthalic acid plant. A portion of the resulting aqueous acetic acid stream is then sent to the azeotropic distillation column (dehydration unit, not illustrated) to remove the water generated in the reaction for recycling or waste.

Typically there are the following aqueous acetic acid streams for feeding to an azeotropic distillation column (dehydration unit): stream 1, condensates from oxidation reactor condensers; stream 2, vapor or condensates from $1^{st}$ and $2^{nd}$ crystallizer; stream 3, solvent stripper OVHD vapor; and stream 4, bottom liquid from high pressure and atmospheric absorbers.

The acetic acid in the streams which contain less than 50 wt % acetic acid can be extracted by liquid-liquid extraction with a solvent, one example of such a process is described by Sasaki et al in U.S. Pat. No. 5,662,780 (1997) in which only one liquid feed with acetic acid concentration 10-50 wt % is allowed to be fed to the liquid-liquid extractor with a solvent 24, which is also used as an entrainer for azeotropic distillation.

Among the above streams, stream 2 includes over 80 wt % of acetic acid and its temperature is too high to send it to extractor 12. As stream 3 is vapor phase, it cannot be sent to extractor 12. Stream 4 containers less than 50 wt % acetic acid and its temperature is lower than 50° C., and so it can be sent to extractor 12. The resulting acetic acid rich solution in the extract 28 then can be separated using azeotropic distillation.

In the case of stream 1, the apparatus for the oxidation process for production of terephthalic acid has typically 3~4 condensers. The condensates from the $1^{st}$ and $2^{nd}$ condensers 78a, 78b contain over 80 wt % of acetic acid, and their temperature is over 160° C. The condensates from the $3^{rd}$ and $4^{th}$ condensers 78c, 78d contain 70~80 wt % of acetic acid and their temperature is 50~70° C.

Less than 50 wt % of acetic acid from condensate from oxidation reactor 76 can be recovered by installing a distillation tower (the water concentrator 90 after the $2^{nd}$ condenser).

Figure 2:
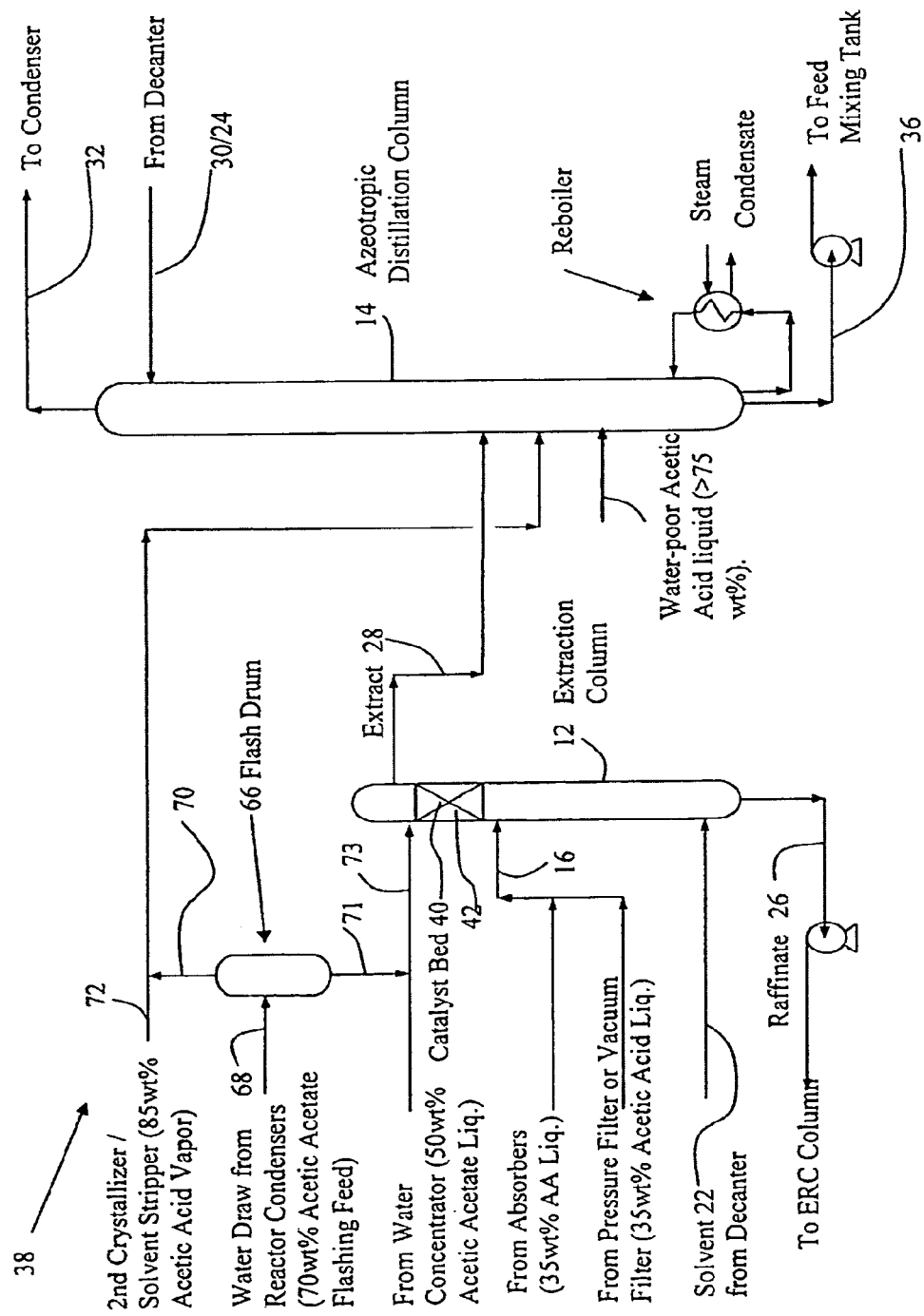
FIG. 2 illustrates a flow diagram of an acetic acid dehydration system according of the invention, incorporating both a guard bed within the extraction column and having two sites for feeding water-poor and water-rich streams at different locations of the azeotropic distillation column.
Figure 3:
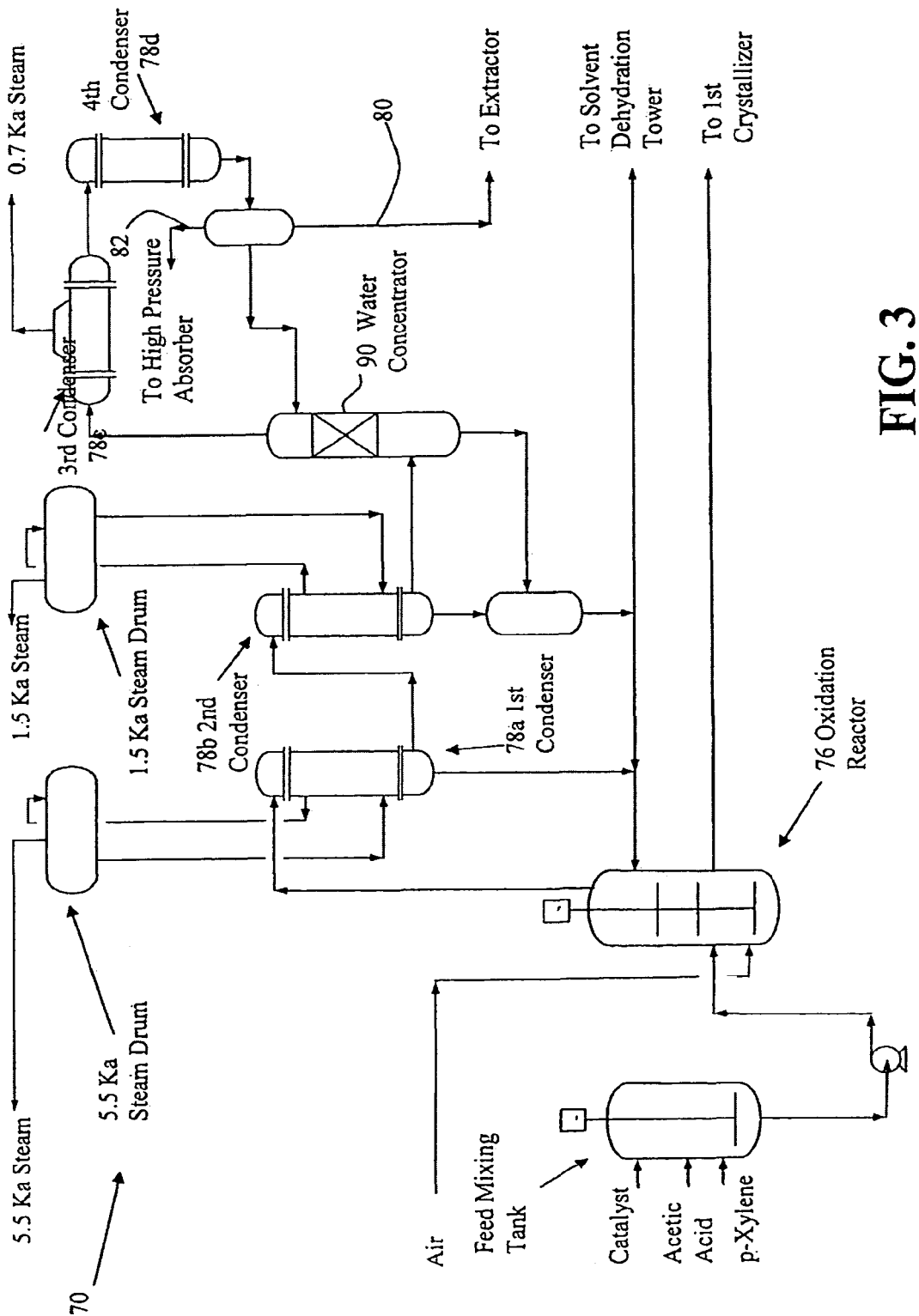
FIG. 3 illustrates a flow diagram for a terephthalic acid manufacturing facility having a water concentrator for production of a stream richer in acetic acid for further processing to recover said acetic acid, wherein the liquid and vapor from the concentrator are respectively fed to the extraction and the azeotropic distillation column as shown in FIG. 2. Optionally, a flash drum is included to partly volatilize acetic acid.

As shown in FIG. 3, overhead vapor from the oxidation reactor is condensed in the $1^{st}$ condenser and $2^{nd}$ condenser. The condensate is recycled back to reactor 76 as reflux and non-condensed vapor is fed to the bottom of the water concentrator 90. The bottom liquid from the water concentrator 90 is recycled to reactor 76 and overhead vapor is sent to $3^{rd}$ and $4^{th}$ condensers. A portion of the condensate 80 (about 50 wt % acetic acid) is sent to extractor 12, as illustrated in FIG. 2, and the rest is recycled back to the water concentrator 90 as reflux. Non-condensed vapor 82 is sent to the high pressure absorber.

As will be described below, extraction solvent 24 is recoverable during further processing for reuse in extraction column 12, to which it may be fed in combination with stream 20.

Referring to FIG. 2, an extraction-azeotropic distillation system 38 for recovery of acetic acid from aqueous solutions from terephthalic acid plants includes an extraction column 12 and an azeotropic distillation column 14. All aqueous acetic acid feed streams at an acetic concentration of 35% may be combined into a single feed stream 16 and fed into extraction column 12 at a site close to the top of the column 12. The extractor shown in FIG. 3 indicates two feed streams at two different concentrations. The invention allows for multiple feeds to the extractor at different locations based on feed stream acetic acid concentrations.

As seen in FIG. 2, optionally a flash drum 66 may be included for phase separation of an acetic acid rich stream 68 into acetic acid vapor 70 and liquid 71. Acetic acid rich liquid 71 can be fed to top of extractor 12 while the vapor 70 can be combined with vapor feed stream 72 and fed directly to azeotropic distillation column 14.

Acetic acid is extracted from feed streams 16 and 73 into extraction solvent 24, thus greatly depleting the concentration of acetic acid in the aqueous component of the mixture in extraction column 12. An acetic acid-depleted aqueous stream 26 exits the bottom of extraction column 12 for further treatment before disposal. The resulting solution 28 containing extraction solvent 24 and acetic acid exits the top of extraction column 12 and toward azeotropic distillation column 14. Solution 28 typically also contains lesser amounts of water and, when extraction solvent 24 is an ester, the corresponding alcohol formed from hydrolysis of the ester (e.g. isopropyl alcohol from isopropyl acetate, or normal butyl alcohol from normal butyl acetate), and may contain other contaminants. Build up of the alcohol and other contaminants is undesirable as they diminish the efficiency of the overall acetic acid recovery process and increase costs resulting from consumption of materials to form waste and necessary purification of effluent streams before disposal.

As seen in FIG. 2, additional water-poor feed streams are fed directly to the azeotropic distillation column at different heights in the column at which the aqueous mixture within said column has a similar water concentration.

Solution 28 is fed into an azeotropic distillation column 14 where it is distilled to separate the majority of the remaining water from the acetic acid. An entrainer 30 is fed near the top of azeotropic distillation column 14. Entrainer 30 forms an azeotropic mixture 32 with water so that the azeotropic mixture 32 is distilled from the top of the column 14. Preferably, entrainer 30 and extraction solvent 24 are the same chemical, and more preferably that chemical is selected from among lower-alkyl esters e.g. normal butyl acetate, isobutyl acetate, normal propyl acetate and isopropyl acetate. An acetic acid rich and water-poor liquid stream 36 is recovered from the bottom of azeotropic distillation column 14.

Azeotropic mixture 32 is condensed and forms two liquid phases which can be separated in a decanter into a water-rich phase which can be further treated before disposal, and a water-poor phase comprising mostly entrainer 30/extraction solvent 24 which can be recycled as stream 22 and reused in extraction column 12, as shown in FIG. 2.

Referring to FIGS. 1 and 2, the deficiencies inherent in prior art acetic acid recovery processes are addressed according to the apparatus and process according to the invention. Common features of prior art apparatus 10 and new apparatus 38 will be identified using the same reference numerals for like parts.

Referring to FIG. 2, in one aspect of the present invention, a guard bed 40 is situated close to the top within extraction column 12. Guard bed 40 contains an esterification catalyst 42 over which acetic acid reacts with alcohol present in the reaction mixture to form the corresponding ester, as illustrated in Equation 1 for the case of normal butyl acetate. Guard bed 40 effects reduction of the amount of alcohol circulating in the system. Alcohol tends to build up during operation of the process. Build up of the amount of alcohol present in the system compromises efficiency of the process by affecting various components: separation of the mixture by distillation in azeotropic distillation column 14; the composition of the azeotrope distilled; and extraction of acetic acid using the entrainer in extraction column 12. Thus operation of each of the major components of the apparatus is deleteriously affected by alcohol build up. Incorporation of guard bed 40 to control alcohol build up thus allows more continuous operation of apparatus 10 in the manner for which it is designed.

Guard bed 40 is situated near the top of extraction column 12 as that is where the concentration of alcohol is highest and the concentration of water is lowest within the column 12, thus favoring ester formation. When guard bed 40 is installed within extraction column 12 the amount of alcohol built up within the system is lower than that in prior art systems. It is an advantage to combine the esterification process and the extraction process within one column 12 to reduce the number of vessels, thus reducing the capital costs and the footprint of the plant, and to thereby treat feed from the extractor directly upon entry into extraction column 12.

In contrast to the present invention, Sasaki et al. in U.S. Pat. No. 5,662,780 (1997) use an external guard bed because the terephthalic acid process for which their invention is designed differs from other terephthalic acid processes in that it has only one aqueous feed stream. Generally, all other terephthalic acid manufacturing plants have multiple aqueous acetic containing streams from different parts of the plant. Thus, for all these other plants, application of the Sasaki '780 invention would require combining of these various streams, which is disadvantageous when compared to the present invention. Combining the acetic acid containing aqueous streams would result in a diluted stream having over 50% water, and so more energy would be required to effect the separation of water and acetic acid from each other.

Reaction 1 is accelerated by using an acidic catalyst such as alumina-HZSM5 or acidic forms of ion exchange resins, for example Amberlyst® 36.

$$n\text{-}C_4H_9OH + HOAc \leftrightarrow n\text{-}C_4H_9OAc + H_2O \quad (1)$$

The equilibrium shown in Equation 1 lies to the right, as shown from the thermodynamic data (Table 1).

TABLE 1

Thermodynamic data for hydrolysis of normal butyl acetate (reverse of Eq. 1)

| Temperature (° C.) | ΔH (kcal) | ΔS (cal/° C.) | ΔG (kcal) | K | Log(K) |
|---|---|---|---|---|---|
| 50 | 0.632 | 0.428 | 0.493 | 4.64E−01 | −0.334 |
| 65 | 0.808 | 0.961 | 0.483 | 4.87E−01 | −0.312 |

The reduction in alcohol content achieved through use of the guard bed within the extraction column is illustrated in Table 2.

TABLE 2

Reduction in concentration of normal butyl alcohol through esterification with acetic acid

| Component | Feed (wt %) | Product (wt %) |
|---|---|---|
| Case 1: Temperature 50° C., high alcohol content | | |
| n-BuOAc | 50 | 67.8 |
| n-BuOH | 30 | 18.7 |
| H$_2$O | 10 | 12.8 |
| HOAc | 10 | 0.823 |
| Case 2: Temperature 65° C., high alcohol content | | |
| n-BuOAc | 50 | 67.7 |
| n-BuOH | 30 | 18.7 |
| H$_2$O | 10 | 12.7 |
| HOAc | 10 | 0.861 |
| Case 3: Temperature 50° C., moderate alcohol content | | |
| n-BuOAc | 70 | 80.2 |
| n-BuOH | 10 | 3.49 |
| H$_2$O | 10 | 11.6 |
| HOAc | 10 | 4.73 |
| Case 4: Temperature 65° C., moderate alcohol content | | |
| n-BuOAc | 70 | 80.0 |
| n-BuOH | 10 | 3.59 |
| H$_2$O | 10 | 11.6 |
| HOAc | 10 | 4.81 |

From Table 2 it can be seen that esterification by reaction with acetic acid greatly reduces the amount of alcohol present in the mixture, thus providing a more appropriate mixture from which acetic acid is extractable under the designed conditions.

Referring to FIG. 1, in another aspect of the present invention, advantage is taken of the different concentrations of water present in different effluent streams originating from the terephthalic acid manufacturing process. Water-rich streams from terephthalic acid plant components: absorbers, water draw distillate and wash water from the press filter(s), may be combined and are fed near the top of extraction column 12.

Water-poor streams from terephthalic acid plant components: wafer drawn from reactor condensers and from crystallizer(s)/solvent strippers, are fed separately to azeotropic distillation column 14. Beneficially, each water-poor stream is fed at a height 50a, 50b, 50c within azeotropic column at which the water concentration is similar to that of the stream, thus minimizing energy requirements to effect the separation of water and extraction solvent containing acetic acid.

The advantages of implementation of the first and second innovations together are:

to reduce the energy required to effect separation of acetic acid from the aqueous feed and to process water before discharging;

to improve the efficiency of operation of the separation process by reducing the amount of undesirable alcohol circulating within the system and so maintain the composition of the mixtures circulating within the apparatus at reasonably consistent levels so as to most closely match the parameters at which the apparatus is designed to operate; and to reduce the amount of waste requiring extraction or destruction before wastes can be eliminated from the plant.

The net effect is a more economical and environmentally more friendly process than prior art systems. The utility and energy savings derived from application of the present invention have been determined, and are summarized in Table 3.

TABLE 3

Comparison of steam consumption for different acetic acid recovery processes.

| Description | Conventional Distillation | Azeotropic Distillation | Sasaki's Patent | | Invention |
|---|---|---|---|---|---|
| Entrainer | No | No | Yes | Yes | Yes | Yes |
| Extraction Solvent | No | No | No | Yes | Yes | Yes |
| Steam Consumption* | 100 | 125 | 70 | 55 | 90 | 55 |
| Acetic Acid Concentration in Waste | 7000 | 1000 | 1000 | 1000 | 1000 | 1000 |
| No of Feeds to Dehydration System | Multiple | Multiple | Multiple | Single | Single | Multiple |
| Feed Condition | Liquid and Vapor | Liquid and Vapor | Liquid and Vapor | Liquid only | Liquid only | Liquid and Vapor |

TABLE 3-continued

Comparison of steam consumption for different acetic acid recovery processes.

| Description | Conventional Distillation | Azeotropic Distillation | Sasaki's Patent | | Invention |
|---|---|---|---|---|---|
| Feed Composition Limititation | No Limit | No Limit | No Limit | Limited to <50 wt % Acetic Acid | Not effective when Acetic | No Limit |
| Recommended Feed Composition | 5 wt %~90 wt % Acetic Acid | 5 wt %~90 wt % Acetic Acid | 5 wt %~90 wt % Acetic Acid | 10 wt %~50 wt % Acetic Acid | Acid >50 wt % | 5 wt %~90 wt % Acetic Acid |

*Calculated based on identical combined feed rates and acetic acid concentration (at 70 wt %) to the Dehydration system.

A further advantage of the present invention is that the distillation apparatus and process described herein are compatible with existing terephthalic acid manufacturing systems so that they may be readily installed to enhance existing plants without large capital expenditures. Catalyst bed 40 is readily installed into extraction column 12. Feed lines for different streams can be installed at the appropriate locations in azeotropic distillation column 14 without compromising components already in place.

It is noteworthy that, as shown in Table 3, the present invention affords operating benefits and cost savings over all prior art processes for recovery of acetic acid from aqueous streams, and in particular for recovery of acetic acid from effluent streams from terephthalic acid manufacturing processes. The steam demand for conventional distillation methods is much higher than that from the present invention, and this is especially so when it is required that the concentration of acetic acid in wastewater is to be no greater than 1000 ppm. Similarly, azeotropic distillation to separate water and acetic acid without prior extraction in an extraction column also requires higher steam demand. The process described by Sasaki et al. in '780 has similar steam demand to that of the present invention, but only when the feed is in the liquid phase and contains less than 50% acetic acid, which does not represent all the acetic acid streams encountered in a typical PTA plant. On the other hand, using the Sasaki's scheme for liquid feed with acetic acid concentration comparable with other cases, i.e. 70 wt %, the process of Sasaki et al. has a higher steam demand. There is no other process described that combines the range of feeds that can be processed and the energy efficiency of the present invention.

Optionally, further benefit can be gained through an additional modification, useful independently of the above innovations, and even more useful when used in combination therewith. The apparatus shown in FIG. 3 is modified as follows. The aqueous effluent stream from second distillation/condensation column 78b of the terephthalic acid manufacturing plant is sent first to a water concentrator 90. A stream richer in acetic acid then is directed to the extractor (extraction column 12, FIG. 2) for extraction of acetic acid and subsequent processing as described above.

The foregoing description of preferred embodiments of the invention is presented for the purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

References Cited
US Patent Documents

| 7,048,835 | May, 2006 | Jang et al. | 203/16 |
| 5,662,780 | September, 1997 | Sasaki et al. | 203/81 |
| 2,395,010 | February, 1946 | Othmer | 260/541 |

US Patent Applications

| PCT/US2006/036963 | September, 2005 | Jang and Wu |

Foreign Patents and Applications

| EP 0 764 627 A1 | March, 1997 | Ohkoshi et al (JP244196/95 (1995)) |

The invention claimed is:

1. A method for recovering acetic acid from an aqueous solution thereof, comprising:
   feeding into a liquid-liquid extraction column a plurality of aqueous liquid input feed streams of different acetic acid concentrations at different locations of the liquid-liquid extraction column based on feed stream acetic acid concentration, including in the liquid-liquid extraction column a guard bed near the top thereof containing a catalyst for esterification of alcohol by reaction with acetic acid to form a corresponding ester,
   feeding into the liquid-liquid extraction column an extraction solvent into which acetic acid is extracted to reduce the concentration of acetic acid, forming a water-rich acetic acid depleted aqueous stream exiting at the bottom of the liquid-liquid extraction column for further treatment and a water-poor fraction containing extraction solvent and water exiting at the top of the liquid-liquid extraction column,
   feeding the water-poor fraction from the liquid-liquid extraction column to an azeotropic distillation column in fluid communication and downstream of the extraction column where the water-poor fraction is distilled to separate a majority of the remaining water from acetic add,
   feeding an entrainer into the azeotropic distillation column to form an azeotropic mixture with water and running the azeotropic distillation column, and
   recovering from the top of the azeotropic distillation column, the azeotropic mixture including water and the entrainer, and from the bottom of the column an acetic acid-rich and water poor liquid stream.

2. A method according to claim 1, comprising before feeding to the liquid/liquid extraction column, the plurality of aqueous liquid acetic acid input feed streams are pre-concentrated in a pre-concentrator, wherein a vapour fraction from the pre-concentrator is partially condensed and is fed to a high pressure absorber, and a portion of a liquid fraction is sent to the liquid-liquid extraction column, while the remainder of the liquid fraction is returned to the pre-concentrator as a reflux.

3. A method according to claim 1, wherein additional water-poor feed streams are fed directly to the azeotropic distillation column, each stream being fed at a height in said column at which the mixture within said column has a similar water concentration.

4. A method according to claim 3, wherein the extraction solvent is a lower-alkyl ester, selected from the group consisting of isobutyl acetate, normal butyl acetate, isopropyl acetate and normal propyl acetate.

5. A method according to claim 4, wherein the entrainer is an ester, selected from the group consisting of isobutyl acetate, normal butyl acetate, isopropyl acetate and normal propyl acetate.

6. A method according to claim 5, wherein the azeotropic mixture is fed to a condenser for receiving the azeotropic mixture, and a portion of a condensate from the condenser is returned to the liquid-liquid extraction column as the extraction solvent.

7. A method according to claim 5, wherein the catalyst for esterification of an alcohol is an acidic catalyst selected from the group consisting of acid forms of aluminosilicate and acid forms of ion exchange resins.

8. A method according to claim 7, wherein the input feed stream is a plurality of liquid feed streams of different acetic acid concentrations, wherein all or portions of the liquid input streams contain acetic acid concentrations of 5-90 wt %.

9. A method according to claim 7, wherein the input feed stream is a plurality of liquid feed streams of different acetic acid concentrations, wherein all or portions of the liquid input streams contain acetic acid concentrations of 5-80 wt %.

10. A method according to claim 1, wherein at least one of the plurality of aqueous acetic acid input feed streams is flashed in a flash drum, and a liquid fraction is fed to the liquid-liquid extraction column, and a vapor fraction is fed to the azeotropic distillation column.

\* \* \* \* \*